United States Patent
Li et al.

(10) Patent No.: US 12,380,559 B2
(45) Date of Patent: *Aug. 5, 2025

(54) SYSTEMS AND METHODS FOR SEGMENTATION OF ANATOMICAL STRUCTURES FOR IMAGE-GUIDED SURGERY

(71) Applicant: INTUITIVE SURGICAL OPERATIONS, INC., Sunnyvale, CA (US)

(72) Inventors: Junning Li, San Jose, CA (US); Pechin Chien Pau Lo, Santa Clara, CA (US); Ahmed Taha, Hyattsville, MD (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,438

(22) Filed: May 24, 2024

(65) Prior Publication Data

US 2024/0312012 A1 Sep. 19, 2024

Related U.S. Application Data

(63) Continuation of application No. 18/299,612, filed on Apr. 12, 2023, now Pat. No. 12,033,325, which is a
(Continued)

(51) Int. Cl.
*A61B 34/20* (2016.01)
*A61B 34/10* (2016.01)
(Continued)

(52) U.S. Cl.
CPC ............ *G06T 7/0012* (2013.01); *A61B 34/10* (2016.02); *A61B 34/20* (2016.02); *G06T 7/12* (2017.01);
(Continued)

(58) Field of Classification Search
CPC ...... A61B 2034/105; A61B 2034/2065; A61B 2034/301; A61B 2090/3735;
(Continued)

(56) References Cited

U.S. PATENT DOCUMENTS 4,736,436 A * 4/1988 Yasukawa ................. G06T 7/00
382/293
9,084,555 B2 7/2015 Lautenschläger
(Continued)

OTHER PUBLICATIONS

Bertasius G., et al., "Semantic Segmentation with Boundary Neural Fields," IEEE Conference on Computer Vision and Pattern Recognition, 2016, pp. 3602-3610.
(Continued)

*Primary Examiner* — Tsung Yin Tsai
(74) *Attorney, Agent, or Firm* — Haynes & Boone, LLP

(57) ABSTRACT

A method for image segmentation comprises receiving volumetric image data for an anatomical region and generating a first volumetric patch from the volumetric image data. The method also comprises generating a second volumetric patch from the first volumetric patch by weighting a plurality of volumetric units in the first volumetric patch and receiving the second volumetric patch as an input to a convolutional neural network. The method also comprises conducting a down-sampling filter process and conducting an up-sampling filter process within the convolutional neural network.

20 Claims, 5 Drawing Sheets

Related U.S. Application Data continuation of application No. 17/122,788, filed on Dec. 15, 2020, now Pat. No. 11,657,502, which is a continuation of application No. 16/289,103, filed on Feb. 28, 2019, now Pat. No. 10,885,630.

(60) Provisional application No. 62/638,831, filed on Mar. 5, 2018, provisional application No. 62/637,232, filed on Mar. 1, 2018.

(51) Int. Cl.
  *G06T 7/00* (2017.01)
  *G06T 7/12* (2017.01)
(52) U.S. Cl.
  CPC ............... *A61B 2034/2065* (2016.02); *G06T 2207/30101* (2013.01)
(58) Field of Classification Search
  CPC ........ A61B 2090/374; A61B 2090/376; A61B 2090/3762; A61B 34/10; A61B 34/20; A61B 34/30; A61B 34/35; A61B 90/37; G06T 2207/10072; G06T 2207/20084; G06T 2207/30084; G06T 2207/30101; G06T 7/0012; G06T 7/11; G06T 7/12; G06T 7/194
  See application file for complete search history.

(56) References Cited

U.S. PATENT DOCUMENTS

| | | | |
|---|---|---|---|
| 9,633,306 B2* | 4/2017 | Liu | G06T 7/0012 |
| 9,760,807 B2 | 9/2017 | Zhou et al. | |
| 9,990,712 B2 | 6/2018 | Gazit | |
| 10,402,975 B2 | 9/2019 | Park et al. | |
| 10,580,141 B2 | 3/2020 | Freiman et al. | |
| 10,825,168 B2 | 11/2020 | Tegzes et al. | |
| 10,885,630 B2* | 1/2021 | Li | G06T 7/0012 |
| 11,657,502 B2 | 5/2023 | Li et al. | |
| 12,033,325 B2 | 7/2024 | Li et al. | |
| 2005/0232474 A1 | 10/2005 | Wei et al. | |
| 2009/0022375 A1 | 1/2009 | Fidrich et al. | |
| 2015/0213613 A1 | 7/2015 | Prevost et al. | |
| 2016/0328643 A1* | 11/2016 | Liu | G06T 7/0012 |
| 2017/0221254 A1 | 8/2017 | Zar et al. | |
| 2017/0228897 A1 | 8/2017 | Holt et al. | |
| 2018/0049721 A1 | 2/2018 | Ben et al. | |
| 2018/0061059 A1 | 3/2018 | Xu et al. | |
| 2018/0218497 A1 | 8/2018 | Golden et al. | |
| 2019/0080456 A1 | 3/2019 | Song et al. | |
| 2019/0251694 A1 | 8/2019 | Han et al. | |
| 2022/0237808 A1 | 7/2022 | Russ et al. | |
| 2023/0252634 A1 | 8/2023 | Li et al. | |
| 2024/0312012 A1* | 9/2024 | Li | A61B 90/37 |

OTHER PUBLICATIONS

Chehab M., et al., "Kidney Imaging," Interventional Urology, Jan. 2016, pp. 221-232.
Chen L.C., et al., "DeepLab: Semantic Image Segmentation with Deep Convolutional Nets, Atrous Convolution, and Fully Connected CRFs," May 2017, 14 Pages.
Cicek O., et al., "3D U-Net: Learning Dense Volumetric Segmentation from Sparse Annotation," Medical Image Computing and Computer-Assisted Intervention, 2016, pp. 424-432.
Cuingnet R., et al., "Automatic Detection and Segmentation of Kidneys in 3D CT Images Using Random Forests," Medical Image Computing and Computer-Assisted Intervention, 2012, vol. 15 (Pt 3), pp. 66-74.
Gomella, L.G., "Combining Artificial Neural Networks and Transrectal Ultrasound in the Diagnosis of Prostate Cancer," Cancer Network, Oct. 2003, vol. 17 (10), 7 pages.
He K., et al., "Deep Residual Learning for Image Recognition," IEEE Conference on Computer Vision and Pattern Recognition (CVPR), 2016, pp. 770-778.
Huang C., et al., "Learning Deep Representation for Imbalanced Classification," IEEE Conference on Computer Vision and Pattern Recognition (CVPR), Jun. 2016, pp. 5375-5384.
Hughes-Hallett A., et al., "Augmented Reality Partial Nephrectomy: Examining the Current Status and Future Perspectives," Urology, Feb. 2014, vol. 83 (2), pp. 266-273.
Ji S., et al., "3D Convolutional Neural Networks for Human Action Recognition" IEEE Transactions On Pattern Analysis And Machine Intelligence, Jan. 2013, vol. 35 (1), pp. 221-231.
Kaiser L., et al., "One Model To Learn Them All," Jun. 2017, 10 pages.
Karpathy A., et al., "Large-scale Video Classification with Convolutional Neural Networks," IEEE Conference on Computer Vision and Pattern Recognition, Jun. 2014, pp. 1725-1732.
Khalifa F., et al., "A Random Forest-based Framework for 3D Kidney Segmentation From Dynamic Contrast-enhanced CT Images," IEEE International Conference on Image Processing, 2016, pp. 3399-3403.
Kingma D.P., et al., "Adam: A Method for Stochastic Optimization," International Conference on Learning Representations, 2015, 15 pages.
Krahenbuhl P., et al., "Efficient Inference in Fully Connected CRFs with Gaussian Edge Potentials," Proceedings of the 24th International Conference on Neural Information Processing Systems, Dec. 2011, pp. 109-117.
Krizhevsky A., et al., "ImageNet Classification with Deep Convolutional Neural Networks," Advances in Neural Information Processing Systems, 2012, pp. 1097-1105.
Milletari F., et al., "V-Net: Fully Convolutional Neural Networks for Volumetric Medical Image Segmentation," 2016, 11 pages.
Ronneberger O., et al., "U-Net: Convolutional Networks for Biomedical Image Segmentation," Medical Image Computing and Computer-Assisted Intervention, 2015, pp. 234-241.
Sharma K., et al., "Automatic Segmentation of Kidneys using Deep Learning for Total Kidney Volume Quantification in Autosomal Dominant Polycystic Kidney Disease," Scientific Reports, May 2017, vol. 7 (1), 10 pages.
Shin H.C., et al., Deep Convolutional Neural Networks for Computer-Aided Detection: CNN Architectures, Dataset Characteristics and Transfer Learning, IEEE Trans Med Imaging, May 2016, vol. 35 (5), 41 pages.
Sorensen T.J., "A Method of Establishing Groups of Equal Amplitude in Plant Sociology Based on Similarity of Species Content and Its Application to Analyses of the Vegetation on Danish Commons," 1948, 46 pages.
Su L.M., et al., "Augmented Reality During Robot-assisted Laparoscopic Partial Nephrectomy: Toward Real-time 3D-CT to Stereoscopic Video Registration," Urology, 2009, vol. 73 (4), pp. 896-900.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Yang G., et al., "Automatic Kidney Segmentation in CT Images based on Multi-atlas Image Registration," International Conference of the IEEE Engineering in Medicine and Biology Society, 2014, vol. 2014, pp. 5538-5541.
Zettinig O., et al., "Multimodal Image-guided Prostate Fusion Biopsy Based on Automatic Deformable Registration," International Journal of Computer Assisted Radiology and Surgery, Dec. 2015, vol. 10 (12), pp. 1997-2007.

* cited by examiner

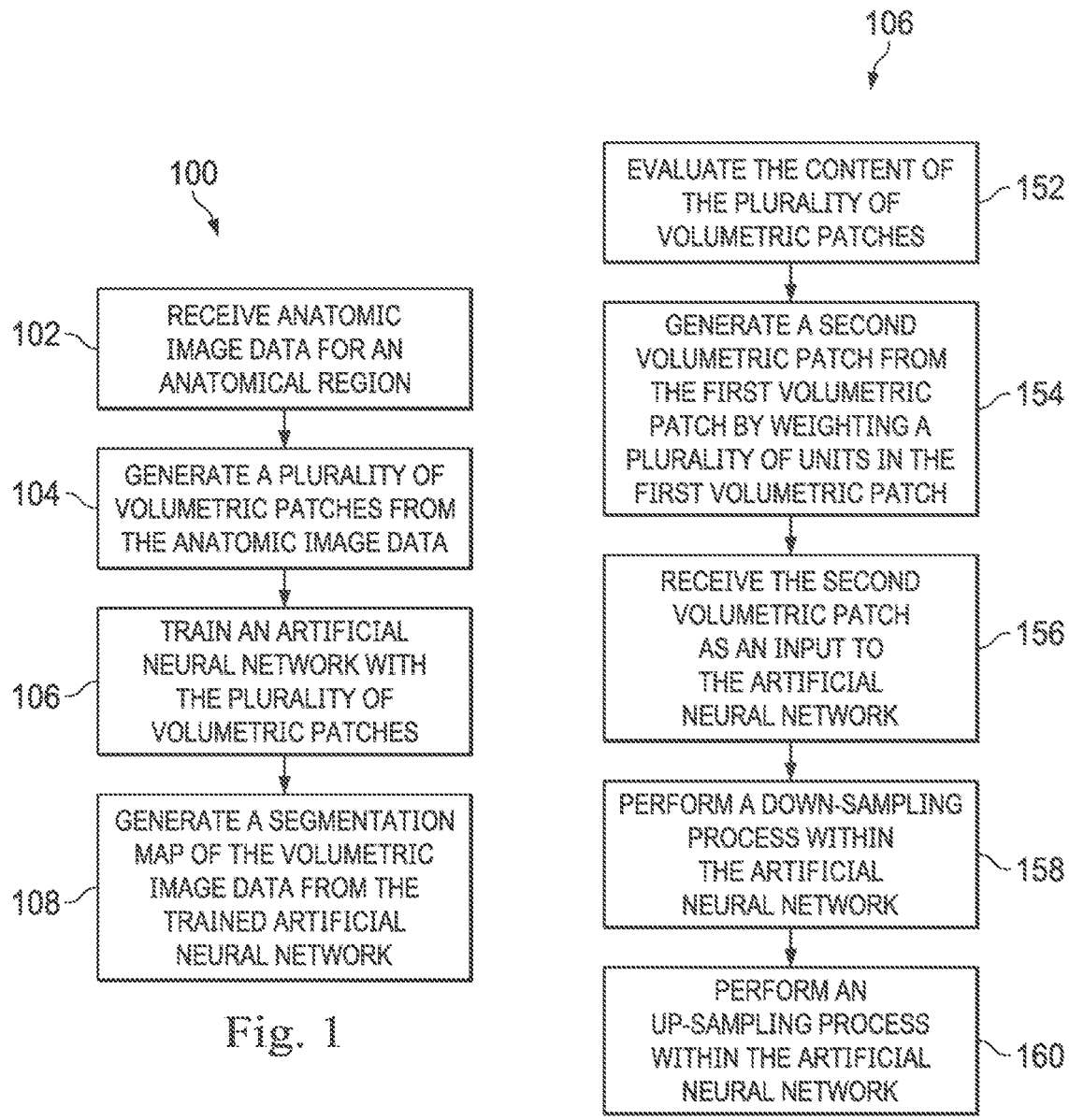

SYSTEMS AND METHODS FOR SEGMENTATION OF ANATOMICAL STRUCTURES FOR IMAGE-GUIDED SURGERY

RELATED APPLICATIONS

This patent application is a continuation of U.S. patent application Ser. No. 18/299,612, filed Apr. 12, 2023, which is a continuation of U.S. patent application Ser. No. 17/122,788, filed Dec. 15, 2020, which is a continuation of U.S. patent application Ser. No. 16/289,103, filed Feb. 28, 2019, which claims priority to and the benefit of the filing date of U.S. Provisional Patent Application No. 62/637,232, entitled "Segmentation of Renal Structures for Image-Guided Surgery," filed Mar. 1, 2018 and of U.S. Provisional Patent Application 62/638,831, entitled "Segmentation of Anatomical Structures for Image-Guided Surgery," filed Mar. 5, 2018, all of which are incorporated by reference herein in their entirety.

TECHNICAL FIELD

The present disclosure is directed to systems and methods for segmenting an anatomic image.

BACKGROUND

Minimally invasive surgical systems enable surgeons to perform minimally invasive surgeries more dexterously and precisely and provide a platform to enable image-guided surgery. For example, a minimally invasive surgical system may include an endoscope held by a teleoperational arm which provides a stable view of the patient anatomy and is tracked in real-time through the robotic kinematics. Images from the endoscope may be augmented with pre-operative or intra-operative images generated by other imaging modalities and displayed to an operator to integrate image information from multiple sources.

Anatomic models generated from pre-operative or intra-operative images, especially three-dimensional models, may illustrate the relationship of the different structures and help with planing the best strategy of the surgery. During the procedure, the model can provide some real-time guidance. For example, by identifying arteries and a tumor, it is possible to find out which major arteries feed the tumor to enable selective arterial clamping. In another example, a model enables the awareness of critical structures (major blood vessels and collecting systems) close to the tumor and helps reduce surgical complications. In another example, images of tumors not visible from outside of an organ are overlaid on the image of the organ to help the surgeons to quickly localize them.

Efficient and low-cost segmentation of anatomical structures is a prerequisite for many image guidance systems. Manual segmentation by using interactive tools can be very time consuming which prohibits the wide spread of such use. Techniques for efficiently segmenting anatomical image data are needed.

SUMMARY

Some embodiments of the invention are best summarized by the claims that follow the description.

Consistent with some embodiments, a method for image segmentation comprises receiving volumetric image data for an anatomical region and generating a first volumetric patch from the volumetric image data. The method also includes generating a second volumetric patch from the first volumetric patch by weighting a plurality of volumetric units in the first volumetric patch and receiving the second volumetric patch as an input to a convolutional neural network. The method also comprises conducting a down-sampling filter process and conducting an up-sampling filter process within the convolutional neural network.

Consistent with some embodiments, a non-transitory machine-readable medium comprises a plurality of machine-readable instructions which, when executed by one or more processors, are adapted to cause the one or more processors to perform a method comprising receiving volumetric image data for an anatomical region and generating a first volumetric patch from the volumetric image data. The method also includes generating a second volumetric patch from the first volumetric patch by weighting a plurality of volumetric units in the first volumetric patch and receiving the second volumetric patch as an input to a convolutional neural network. Within the convolutional neural network, a down-sampling filter process and an up-sampling filter process are conducted.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 1 illustrates a method for image segmentation according to some embodiments.

FIG. 4 illustrates a method for training an artificial neural network according to some embodiments.

Figure 3A:
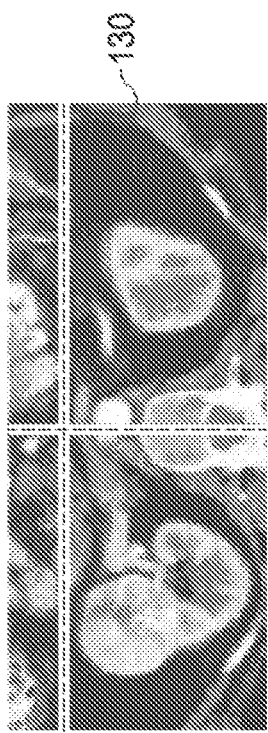
FIG. 3A illustrates an anatomic image generated from anatomic image data according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

FIG. 1 illustrates a method 100 for image segmentation according to some embodiments. The method 100 is illustrated as a set of operations or processes 102 through 108. Not all of the illustrated processes 102 through 108 may be performed in all embodiments of method 100. Additionally, one or more processes that are not expressly illustrated in FIG. 1 may be included before, after, in between, or as part of the processes 102 through 108. In some embodiments, one or more of the processes may be implemented, at least in part, in the form of executable code stored on non-transitory, tangible, machine-readable media that when run by one or more processors may cause the one or more processors to perform one or more of the processes.

Figure 2A:
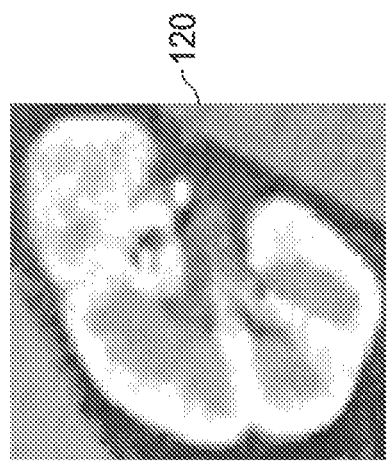
FIG. 2A illustrates an anatomic image generated from anatomic image data according to some embodiments.

At a process 102, anatomic image data for an anatomical region is received by a processor. Various imaging techniques may be used to acquire anatomical image data of a patient anatomy for use in a variety of medical procedures including surgical, diagnostic, therapeutic procedures. For example, anatomical image data may be acquired using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Anatomical image data may be acquired preoperatively or intraoperatively. In some embodiments, the anatomic image data may be volumetric image data representing a three-dimensional model of a patient anatomic region. With reference to FIGS. 2A and 3A, anatomic images 120, 130 may be generated from anatomic image data such as CT image data. Although the illustrations of this disclosure may refer to anatomical structures of the kidney, the systems and methods described herein may be applied to other anatomical regions including the lung, the heart, the colon, the intestines, the brain, the circulatory system including vasculature, and/or the like.

At a process 104, training patches are generated from the anatomic image data. The training patches are comprised of a plurality of graphical units (e.g. pixels or voxels). In some embodiments the training patches are three-dimensional volumetric patches comprised of a plurality of voxels. In one embodiment, for example, each training patch may have a 96×96×96 voxel dimension.

At a process 106, all or some subset of the training patches may be used as inputs to train an artificial neural network. The artificial neural network may be, for example, a deep convolutional neural network, including multiple convolution layers with each layer including a convolution filter kernel. In these layers, the filter kernels are applied to the input patches to thereby perform a convolution operation and generate a feature map. The convolution operation may be followed by a pooling operation to reduce the dimensionality of the feature map. In some embodiments, the artificial neural network may be a U-shaped network that performs down-sampling filter operations to detect features within the anatomical image data and up-sampling filter operations (i.e., deconvolution) to localize the detected features by assigning classification information to the detected features.

Figure 3B:
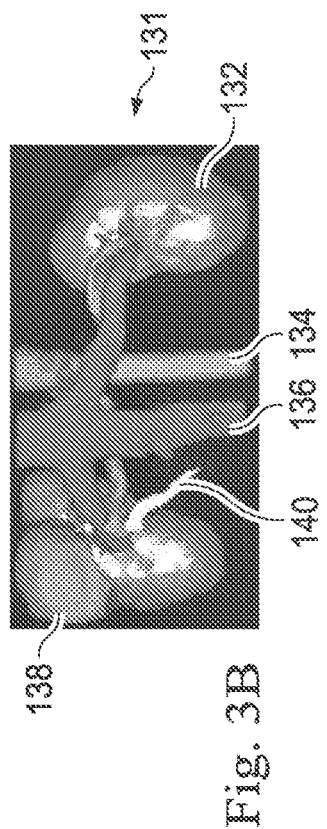
FIGS. 3B and 3C illustrate the anatomy of FIG. 2A with segmented and localized anatomical features according to some embodiments.
Figure 3C:
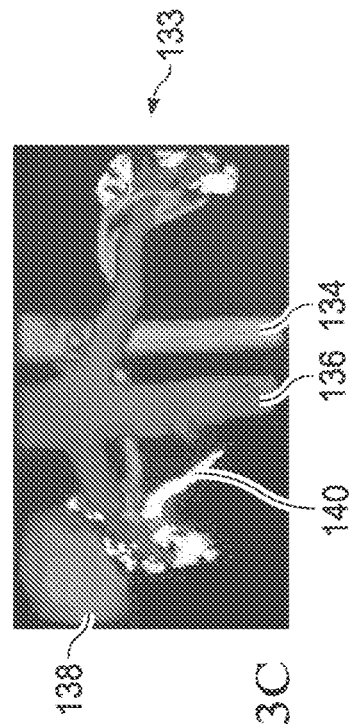
Figure 2B:
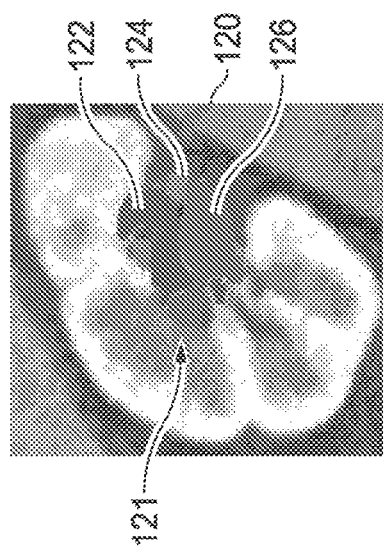
FIG. 2B illustrates the anatomic image of FIG. 2A with segmented and localized anatomical features according to some embodiments.

At a process 108, one or more segmentation maps are generated by the trained convolutional neural network. The output segmentation maps include segmented anatomical features. In some embodiments the output segmentation maps may displayed on a display system. In some embodiments, the output segmentation maps may be displayed with the anatomic image data. For example, in some embodiments, all or some of the segmented anatomical features may be superimposed on the anatomic image data or displayed side-by-side with the anatomic image data. With reference to FIGS. 2B, 3A, and 3B, segmentation maps 121, 131, 133 are generated from trained convolutional neural networks. The segmentation map 121 is generated from the anatomic image 120. Segmented anatomical features include arteries 124, veins 122, and ureter tissue 126. In this embodiment, the segmented anatomical features 124, 122, 126 are displayed with the anatomic image 120. The segmentation maps 131, 133 are generated from the anatomic image data used to generate anatomic image 130. The segmentation map 133 includes the segmented anatomical features of parenchyma tissue 132, arteries 134, veins 136, masses 138 including abnormal tissue such as tumors, kidney stones, or cysts, and ureter tissue 140. In some embodiments, the displayed segmentation map may omit certain ones of the segmented features. For example, the segmentation map 133 may omit the parenchyma tissue 132 to allow the viewer to better observe the ureter tissue structure 140.

FIG. 4 illustrates, in greater detail, the process 106 for training an artificial neural network according to some embodiments. The process 106 is illustrated as a set of operations or sub-processes 152 through 160. Not all of the illustrated sub-processes may be performed in all embodiments of process 106. Additionally, one or more sub-processes that are not expressly illustrated in FIG. 4 may be included before, after, in between, or as part of the sub-processes 152 through 160. In some embodiments, one or more of the sub-processes may be implemented, at least in part, in the form of executable code stored on non-transitory, tangible, machine-readable media that when run by one or more processors may cause the one or more processors to perform one or more of the sub-processes.

In some embodiments, all or a randomly generated subset of the plurality of volumetric patches may be used to train the artificial neural network. The patches and/or the voxels within the patches may be uniformly weighted such that no particular consideration is given to the content of the patches and voxels. This type of uniform weighting in model training may yield unsatisfactory segmentation results. For example, it will tend to label voxels into some classifications at percentages overwhelmingly greater than other classifications. Besides this inter-class unbalance, it may also create problems for intra-class voxels. For example, it will undesirably make small anatomical structures (e.g., thin vessels) less important than larger anatomical structures (e.g., thick vessels) simply because the smaller anatomical structures are comprised of fewer voxels. As described below, various techniques may be used to assign weights to voxels, groups of voxels, or entire patches to ensure the artificial neural network is trained to balance foreground and background classifications, emphasize structure edges, and emphasize complicated or detailed anatomical structures. Foreground classifications may be associated with anatomical structures of greatest interest. In the kidney for example, foreground classifications may be assigned to anatomical structures such as parenchyma tissue, ureter tissue, arteries, veins, and masses including abnormal tissue such as tumors, kidney stones, or cysts.

Figure 5:
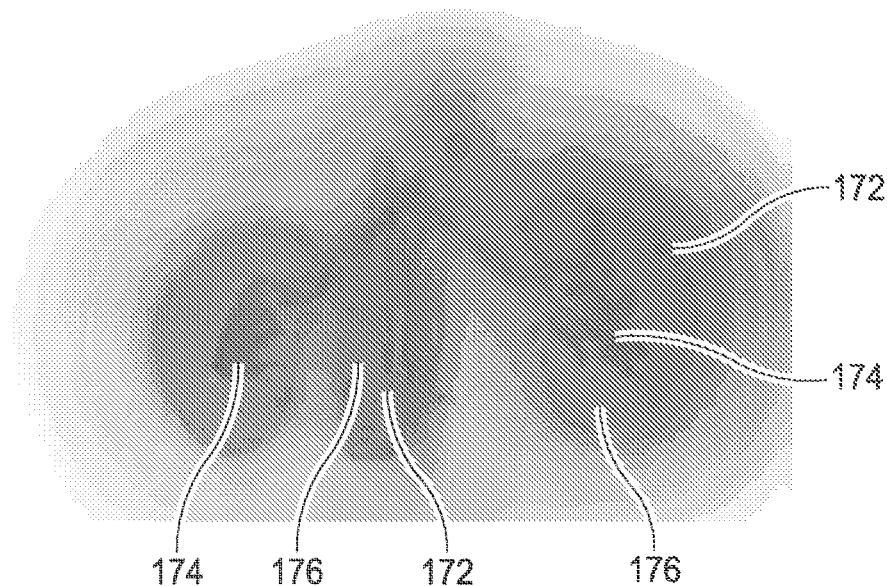
FIG. 5 illustrates a multi-scale entropy map of anatomical features according to some embodiments.

At a sub-process 152, the content of the plurality of volumetric patches may be evaluated to determine weights for the voxels in each patch. In one embodiment and with reference to FIG. 5, a multi-scale categorical entropy map 170 is generated. The voxels associated with high entropy properties may be evaluated to have a greater value and therefore, be assigned a higher weighting. The voxel-wise weight map 170 may emphasize any of a variety of properties. For example, in the map 170 edges 172 may be important as they define a boundary. Complicated structures 174 (e.g., branching thin vessels), though possibly small, may be important as they indicate the source of blood flow to tissues. Additionally, the farther away a point is from the foreground, the less important it may be. The entropy map generally provides an indication of structural detail between scale levels. For example, if the difference in detail between scale levels is great (e.g., great detail in foreground structures between zoom resolution levels), entropy is high. If the difference in detail between scale levels is small (e.g., all background between zoom resolution levels) entropy is low.

Given a multi-channel probabilistic map y and a series of increasing scale levels $\sigma_0, \ldots, \sigma_n$, the multi-scale entropy s is defined as:

$$y_\sigma = \kappa_\sigma * y, \text{ for } \sigma \in \{\sigma_0, \ldots, \sigma_n\}, \quad (1)$$

$$RelativeEntropy_{\sigma_i|\sigma_{i+1}}(p) = \sum_c y_{\sigma_i}(p)[c]\frac{y_{\sigma_i}(p)[c]}{y_{\sigma_{i+1}}(p)[c]}, \quad (2)$$

$$s_{\sigma_i|\sigma_{i+1}} = \kappa_{|\sigma_{i+1}-\sigma_i|} * RelativeEntropy_{\sigma_i|\sigma_{i+1}}, \quad (3)$$

$$s = \sum_i s_{\sigma_i|\sigma_{i+1}}. \quad (4)$$

where $\kappa_\sigma$, is a Gaussian kernel of width $\delta$, and $y_{\sigma i}(p)[c]$ is c-th channel's probability at a point p in $y_{\sigma i}$. Equation (1) generates a series of smoothed probabilistic maps ys s from the original map y. Equation (2) calculates the relative entropy between two smoothed probabilistic maps $y_{\sigma i}$ and $y_{\sigma i+1}$. It captures how complex the label map is at a scale. Equation (3) smooths the relative entropy map to the resolution of $\sigma_{0i+1}$. Equation (4) sums up relative entropy at different scales. $\sigma_0, \ldots, \sigma_n$ usually increase exponentially. The entropy map 170 shows an entropy map derived at $\sigma=1$, 2, 4, 8, 16, 32, 64, 128, and 256, emphasizing edges 172, complicated structures 174 and areas near the foreground 176.

In another embodiment, voxels associated with certain foreground classifications may be evaluated to have a greater value and therefore, be assigned a higher weighting. Both intra-foreground and background-foreground classes may be balanced within volumetric patches. In many embodiments, a majority of patches are free of foreground structures. Even when a foreground class exists, it occupies a small percentage. To hinder bias against the foreground classes, voxels may be weighted based on their classification and/or based on patch significance. A major challenge in medical image processing is detecting small structures. Vessels in direct contact with organs are tiny and their resolution is limited by acquisition. Tiny vessels are challenging to annotate and more valuable to acquire. Thus, patches containing smaller foreground structures such as vessels are more significant and may be assigned a higher weight. Patch weight may be inversely proportional to the foreground structure volume (e.g., vessel volume) inside the patch. Foreground classes may also be assigned higher weights to hinder the network background bias. During the evaluation sub-process 152 the average foreground class volumes may be dynamically measured per patch. Then, higher weights may be assigned to classes with smaller average volumes and vice versa.

In one embodiment, a policy that a vessel volume×weight must equal 1/n is imposed where n is the number of classes including the background class. Thus, all classes contribute equally from a network perspective. To account for data augmentation, vessel volumes are measured during training Enforcing equal contribution (volume×weight) from all classes may be an objective. To do so, a moving average procedure may be used:

---

Algorithm 1
Our proposed moving average procedure assigns voxels dynamic weights ($VW_c$) based on their classes and patch weight. Patch Weight (PW) is inversely proportional to its foreground volume.
Class weight (CW) is inversely proportional to its average volume per patch; initially $V_c = \frac{1}{n}$ for every class c.

Our settings $\alpha = 0.001$, n = 4.

---

Require: α: Convergence Rate
Require: P: Current 3D patch with axis x, y, z
Require: n: Number of classes (background included)
Require: $V_c$: Class (c) moving average volume
Require: PW: Current patch weight
Require: $CW_c$: Class (c) weight
  for all c in classes do
  // Measure class (c) volume in patch P
  $V_c(P) = (\Sigma_x \Sigma_y \Sigma_z P(x, y, z) == c) / size(P)$
  // Update class (c) moving average volume
  $V_c = V_c \times (1 - a) + V_c(P) \times a$
  // Update class weight based on its moving average volume
  $CW_c = 1/ (n \times V_c)$
  end for
  // Set patch weight based on foreground volume
  If P contains background only then
    PW = 1
  else
    // Foreground volume $\Sigma_{c=1}^{n-1} V_c(P) < 1$
    PW = $1 - \log(\Sigma_{c=1}^{n-1} V_c(P))$
  end if
  $VW_c$ = PW * $CW_c$ (Voxel weight is function of PW and $CW_c$)

---

Figure 6:
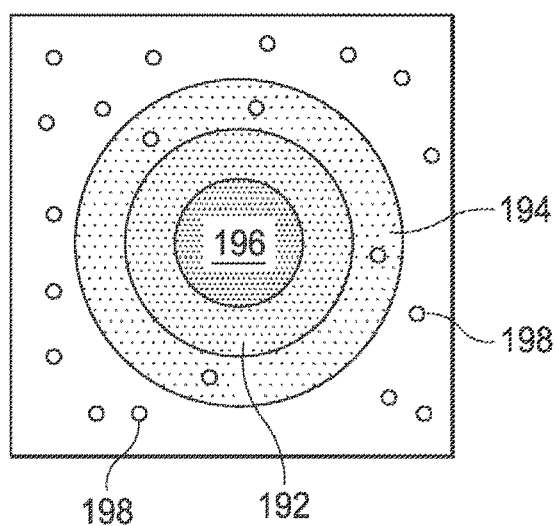
FIG. 6 illustrates a background sampling approach according to some embodiments.

Because a large volume of voxels have background classifications, those voxels may be assigned a small class weight. Consequently, many of false classifications may be generated because it is relatively cheap to mis-classify a background voxel. To overcome this undesired phenomena, a random background sampling technique may be used to weight background voxels. With this technique, background voxels are sampled at random and assigned high weights. This technique may be effective in limiting false positives because a high loss is incurred for these mis-classified voxels. With reference to the sampling schema 190 of FIG. 6, a band 192 and a band 194 are constructed around a foreground anatomical structure 196 (e.g., a vessel) using morphological kernel, a binary circular radial distance of two and four voxels. Misclassifications within the band 192 (e.g., <2 voxels away from the vessel) are considered marginal errors. In a given patch, sampled background voxels 198 are equivalent to the foreground vessel volume, where 20% and 80% come from the band 194 and the volume beyond this band respectively. If a patch is free foreground voxels, 1% of the background voxels are randomly sampled.

With reference again to the process 106 of FIG. 4, at a sub-process 154, any of the weighting schema described above may be applied to the voxels in each patch to be used for training the artificial neural network. The weighted volumetric patch generated by weighting the first volumetric patch may be considered a second volumetric patch.

At a sub-process 156 the weighted volumetric patches may be input to the convolutional filters of the artificial neural network. In various embodiments, the artificial neural network may be a convolutional neural network such as a residual UNet.

At a process 158, the residual UNet performs down-sampling procesesses as described below. At a process 160, the residual UNet performs an up-sampling process and described below.

In greater detail with regards to the residual UNet architecture, a residual architecture for directed acyclic graphs is fully compatible with a sequential residual network. Within the residual architecture, let G={V, E} be a directed acyclic graph where V is its vertices and E is its directed edges. Given a vertex α∈V, let ancestors (α), excluding a itself, denote the vertices in V which can reach a via directed paths in E. The residual graph derived from G is composed by functions on vertices. The function $F_a$ on a vertex α takes the summation of ancestors (α) as its input, that is:

$$\text{input of } f_a = \sum_{b \in ancestors(a)} f_b$$

Figure 7:
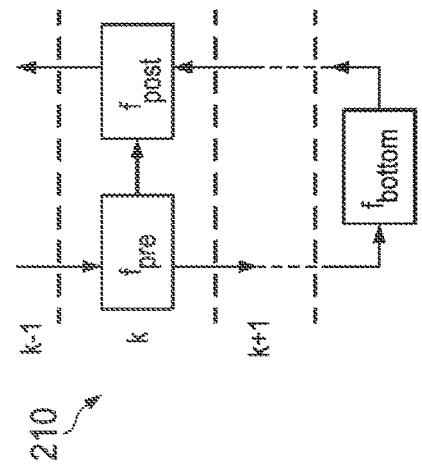
FIG. 7 illustrates a residual architecture for a directed acyclic graph according to some embodiments.

FIG. 7 illustrates a residual graph 200 where the input of f4 is the summation of f1 and f2; the input of f5 is the summation of f2 and f3; and the input of f6 is the summation of f1, f2, . . . , f5.

Figure 8:
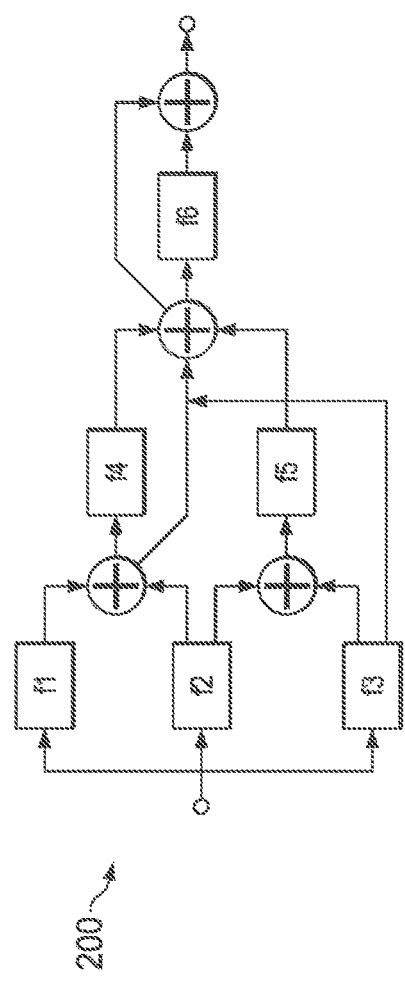
FIG. 8 illustrates a UNet architecture according to some embodiments.

In various embodiments, UNet used for image segmentation is a deep neural network using multi-scale analysis. FIG. 8 illustrates the UNet architecture 210 according to some embodiments. In this embodiment, an image is processed at different scales. At one scale k, there are two filters $f_{pre}$ and $f_{post}$. The filter $f_{pre}$ takes its input from a lower scale k−1, and then relays its output to a higher scale k+1. (Shifting from low scales to high scales is implemented by down-sampling or strided convolution.) In this way, features are summarized from low scales to high scales. The filter $f_{post}$ takes its input from both $f_{pre}$ and a higher scale k+1 and relays its output to a lower scale k−1. (Shifting from high scales to low scales is implemented by up-sampling or deconvolution convolution.) In this way, local information is combined with high scale context information.

Figure 9:
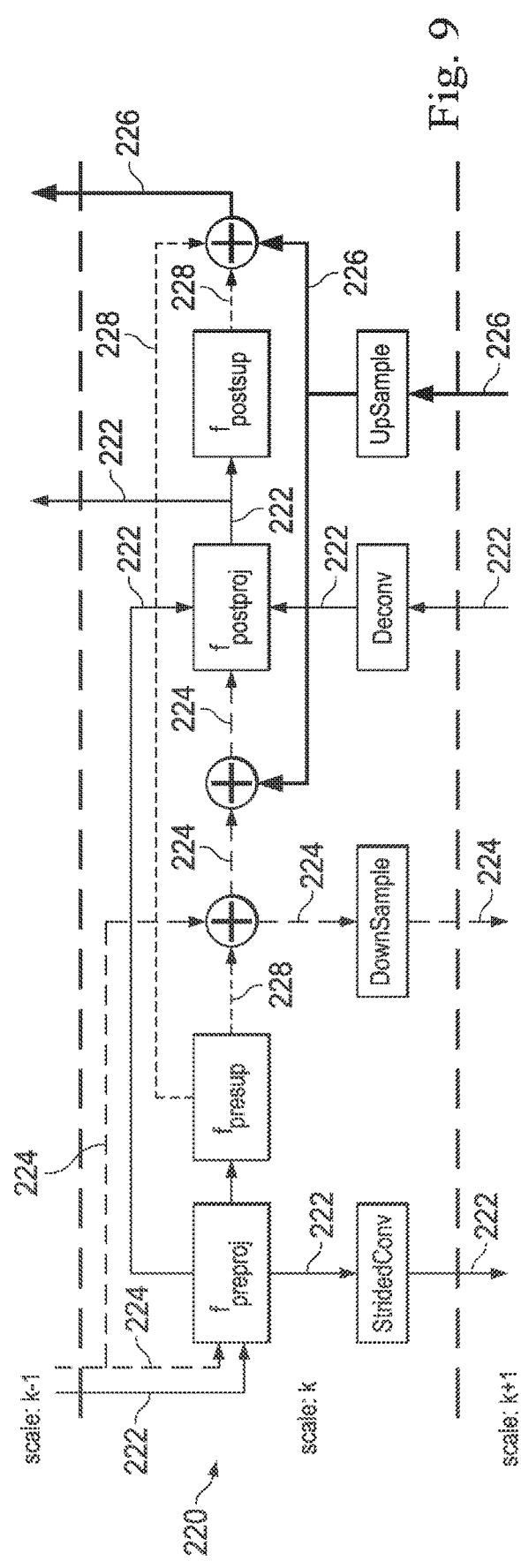
FIG. 9 illustrates a residual UNet architecture according to some embodiments.
Figure 10:
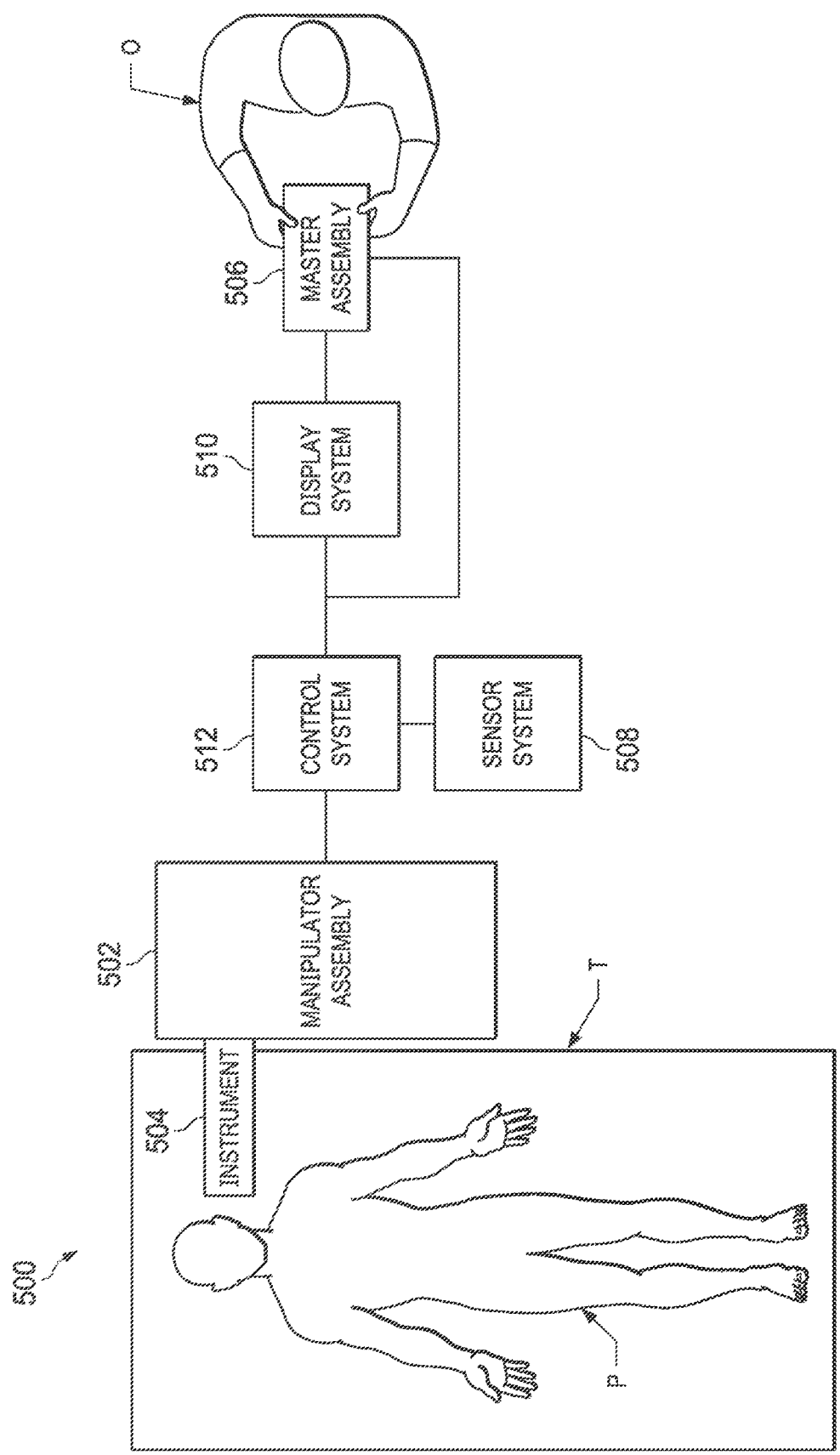
FIG. 10 illustrates a simplified diagram of a robotic or teleoperated medical system according to some embodiments.

FIG. 9 illustrates a ResUNet architecture 220 which includes aspects of the residual graph 200 with the UNet architecture 210. Data flows from low scales to high scales through two channels: channel 222 which is scale-specific features and channel 224 which is the accumulation of supervision features. The channels 222, 224, concatenated together, are projected to a high-dimensional feature space through $f_{preproj}$ and then compressed by $f_{prepsup}$. The output of $f_{prepsup}$ is added to the channel 224 to keep the accumulation updated. The channels 222, 224, after $f_{preproj}$ and $f_{prepsup}$, are forwarded to a higher scale k+1, respectively through strided convolution and down-sampling. Data flows from high scales to low scales through 222 and channel 226, respectively through de-convolution and up-sampling. The channel 226 is the accumulation of features from the last scale to the current scale k. The channel 226 is added to the channel 224 to keep the accumulation updated. The accumulated features, concatenated with the channels 222, are projected to a high-dimensional feature space through $f_{postproj}$, and then compressed by $f_{postsup}$. The outputs of $f_{presup}$ and $f_{postsup}$ added to the channel 226 to keep it as the accumulation from the current scale to the last scale. When the channel 226 travels to the first scale, it is the accumulation of all scales.

The ResUNet architecture 220 consists of two threads. The first thread is scale-specific features: the channels 222. It follows a similar architecture to the UNet architecture 210. It branches at $f_{preproj}$ and then merges at $f_{postproj}$. The second thread is the residual architecture, including the channels 224, 226, 228. The pair of $f_{preproj}$ and $f_{prepsup}$ and the pair of $f_{presup}$ and $f_{postsup}$ are considered as processing units in the residual architecture. $f_{presup}$ and $f_{postsup}$ produces the output of a processing unit. $f_{preproj}$ or $f_{postproj}$ only produces intermediate features. The input to a processing unit always includes summation of $f_{presup}$ or $f_{postsup}$ from its ancestor processing units.

In some embodiments, image segmentation may be used in an image-guided medical procedure performed with a teleoperated medical system as described in further detail below. While some embodiments are provided herein with respect to such procedures, any reference to medical or surgical instruments and medical or surgical methods is non-limiting. In some embodiments, the segmented tree structures may be used for non-teleoperational procedures involving guidance of traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems. As shown in FIG. 7, medical system 500 generally includes a manipulator assembly 502 for operating a medical instrument 504 in performing various procedures on a patient P positioned on a table T. The manipulator assembly 502 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 506 generally includes one or more control devices for controlling manipulator assembly 502. Manipulator assembly 502 supports medical instrument 504 and may optionally include a plurality of actuators or motors that drive inputs on medical instrument 504 in response to commands from a control system 512. The actuators may optionally include drive systems that when coupled to medical instrument 504 may advance medical instrument 504 into a naturally or surgically created anatomic orifice. Other drive systems may move the distal end of medical instrument 504 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 504 for grasping tissue in the jaws of a biopsy device and/or the like.

Teleoperated medical system 500 also includes a display system 510 for displaying an image or representation of the surgical site and medical instrument 504 generated by subsystems of sensor system 508. Display system 510 and master assembly 506 may be oriented so operator O can control medical instrument 504 and master assembly 506 with the perception of telepresence.

In some embodiments, medical instrument 504 may include components of an imaging system, which may include an imaging scope assembly or imaging instrument that records a concurrent or real-time image of a surgical site and provides the image to the operator or operator O through one or more displays of medical system 500, such as one or more displays of display system 510. The concurrent image may be, for example, a two or three-dimensional image captured by an imaging instrument positioned within the surgical site. In some embodiments, the imaging system includes endoscopic imaging instrument components that may be integrally or removably coupled to medical instrument 504. However, in some embodiments, a separate endoscope, attached to a separate manipulator assembly may be used with medical instrument 504 to image the surgical site. The imaging system may be implemented as hardware, firmware, software or a combination thereof which interact with or are otherwise executed by one or more computer processors, which may include the processors of the control system 512.

Teleoperated medical system 500 may also include control system 512. The artificial neural network may operate within the control system 112. Control system 512 includes at least one memory and at least one computer processor (not shown) for effecting control between medical instrument 504, master assembly 506, sensor system 508, and display system 510. Control system 512 also includes programmed instructions (e.g., a non-transitory machine-readable medium storing the instructions) to implement some or all of the methods described in accordance with aspects disclosed herein, including instructions for providing information to display system 510.

Control system 512 may optionally further include a virtual visualization system to provide navigation assistance to operator O when controlling medical instrument 504 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein. In some instances well known methods, procedures, components, and circuits have not been described in detail so as not to unnecessarily obscure aspects of the embodiments.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A method for image segmentation, the method comprising:
   receiving volumetric image data for an anatomical region;
   generating a first volumetric patch from the volumetric image data;
   generating a second volumetric patch from the first volumetric patch by weighting a plurality of volumetric units in the first volumetric patch, wherein weighting the plurality of volumetric units includes applying a weight based on a patch significance for the first volumetric patch;
   receiving the second volumetric patch as an input to a convolutional neural network;
   within the convolutional neural network, conducting a down-sampling filter process; and
   within the convolutional neural network, conducting an up-sampling filter process.

2. The method of claim 1 wherein weighting the plurality of volumetric units includes using a multi-scale entropy map to weight the plurality of volumetric units.

3. The method of claim 2 wherein weighting at least one of the plurality of volumetric units includes applying a weight based on edge features identified in the multi-scale entropy map.

4. The method of claim 2 wherein weighting at least one of the plurality of volumetric units includes applying a weight based on structure complexity identified in the multi-scale entropy map.

5. The method of claim 2 wherein weighting at least one of the plurality of volumetric units includes applying a weight based on a distance of the at least one of the plurality of volumetric units from a volumetric unit with a foreground structure classification in the first volumetric patch.

6. The method of claim 1 wherein weighting the plurality of volumetric units includes applying a weight based on a foreground structure classification.

7. The method of claim 6 wherein volumetric units nearer a volumetric unit with the foreground structure classification are associated with a weight greater than volumetric units more remote from the volumetric unit with the foreground structure classification.

8. The method of claim 1 wherein weighting the plurality of volumetric units includes
identifying a set of the plurality of volumetric units that have a background structure classification and
applying a weight to a randomly selected volumetric unit of the set of the plurality of volumetric units.

9. The method of claim 1 wherein conducting the down-sampling filter process includes applying a first filter at a first resolution scale to generate a first output and applying a second filter to the first output at a second resolution scale.

10. The method of claim 9 wherein conducting the up-sampling filter process includes applying a third filter to the first output at the first resolution scale and to an output of the second filter at the second resolution scale.

11. A non-transitory machine-readable medium comprising a plurality of machine-readable instructions which, when executed by one or more processors, are adapted to cause the one or more processors to perform a method comprising:
receiving volumetric image data for an anatomical region;
generating a first volumetric patch from the volumetric image data;
generating a second volumetric patch from the first volumetric patch by weighting a plurality of volumetric units in the first volumetric patch, wherein weighting the plurality of volumetric units includes applying a weight based on a patch significance for the first volumetric patch;
receiving the second volumetric patch as an input to a convolutional neural network;
within the convolutional neural network, conducting a down-sampling filter process; and
within the convolutional neural network, conducting an up-sampling filter process.

12. The non-transitory machine-readable medium of claim 11 wherein weighting the plurality of volumetric units includes using a multi-scale entropy map to weight the plurality of volumetric units.

13. The non-transitory machine-readable medium of claim 12 wherein weighting at least one of the plurality of volumetric units includes applying a weight based on edge features identified in the multi-scale entropy map.

14. The non-transitory machine-readable medium of claim 12 wherein weighting at least one of the plurality of volumetric units includes applying a weight based on structure complexity identified in the multi-scale entropy map.

15. The non-transitory machine-readable medium of claim 12 wherein weighting at least one of the plurality of volumetric units includes applying a weight based on a distance of the at least one of the plurality of volumetric units from a volumetric unit with a foreground structure classification in the first volumetric patch.

16. The non-transitory machine-readable medium of claim 11 wherein weighting the plurality of volumetric units includes applying a weight based on a foreground structure classification.

17. The non-transitory machine-readable medium of claim 16 wherein volumetric units nearer a volumetric unit with the foreground structure classification are associated with a weight greater than volumetric units more remote from the volumetric unit with the foreground structure classification.

18. The non-transitory machine-readable medium of claim 11 wherein weighting the plurality of volumetric units includes
identifying a set of the plurality of volumetric units that have a background structure classification and
applying a weight to a randomly selected volumetric unit of the set of the plurality of volumetric units.

19. The non-transitory machine-readable medium of claim 11 wherein conducting the down-sampling filter process includes applying a first filter at a first resolution scale to generate a first output and applying a second filter to the first output at a second resolution scale.

20. The non-transitory machine-readable medium of claim 19 wherein conducting the up-sampling filter process includes applying a third filter to the first output at the first resolution scale and to an output of the second filter at the second resolution scale.

* * * * *